United States Patent [19]

Trivedi

[11] Patent Number: 4,714,697
[45] Date of Patent: Dec. 22, 1987

[54] N6-BICYCLOADENOSINES AND METHODS OF USE
[75] Inventor: Bharat Trivedi, Canton, Mich.
[73] Assignee: Warner Lambert Company, Morrisplains, N.J.
[21] Appl. No.: 772,983
[22] Filed: Sep. 9, 1985
[51] Int. Cl.$^4$ .................. A61K 31/70; C07H 19/167
[52] U.S. Cl. ........................ 514/46; 514/45; 536/24; 536/26
[58] Field of Search .............. 536/24, 26; 514/45, 514/46

[56] References Cited

U.S. PATENT DOCUMENTS 3,838,147  9/1974  Pohlke et al. ................ 536/26
3,840,521  10/1974  Fauland et al. .............. 536/26
4,210,639  7/1980  Chiang et al. ................ 536/24

FOREIGN PATENT DOCUMENTS 40325  11/1981  European Pat. Off. ........ 536/26
2249397  5/1974  Fed. Rep. of Germany ... 536/26

Primary Examiner—Johnnie R. Brown
Assistant Examiner—L. Eric Crane

[57]  ABSTRACT

N$^6$-Bicyclo adenosines and pharmaceutically acceptable acid addition salts having highly desirable antiinflammatory and analgesic activity and processes for their manufacture as well as pharmaceutical compositions and methods for using said compounds and compositions are described.

14 Claims, No Drawings

N6-BICYCLOADENOSINES AND METHODS OF USE

BACKGROUND OF THE INVENTION

German Pat. No. 2,249,396 and European Patent Publication 40325 disclose N6-bicycloalkyl adenosine derivatives having circulatory, antilipolytic, anticonvulsant, muscle relaxant, and sedative activity. U.S. Pat. No. 3,840,521 discloses N6-methyl-N6-[bicyclo(2.2.1)-heptyl-2]adenosine having antilipolytic, antihyperlipemic, and antihypercholesterolemic activity.

The compounds of the instant invention are adenosine analogs having some of the same activity as adenosine, but having a significantly longer duration of action. A distinguishing feature of these compounds from other adenosine analogs previously described, is the discovery that N6-bicycloadenosines have favorable ratio of affinities at A1 and A2 receptors and highly desirable analgesic and antiinflammatory properties.

SUMMARY OF THE INVENTION

Accordingly the present invention relates to compound of the formula

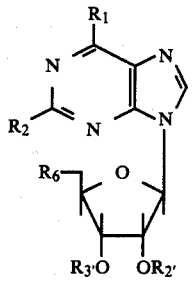

I wherein $R_1$ is of formula

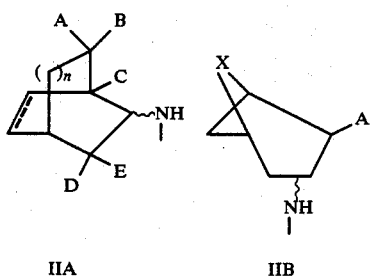

in which ~NH— is either endo or exo; ------- is a double or single bond; n is zero, one, or two; A and B are either both hydrogen or both methyl; D and E are also either both hydrogen or both methyl; C is hydrogen or methyl; and with the proviso that when D and E are methyl then A and B are both hydrogen and C is methyl, but when D ane E are hydrogen then A, B, and C are all hydrogen or all methyl; X is —C(CH3)2—, —CH2—, —CH2—CH2—, —CH=CH—. $R_2$ is hydrogen, halogen, SR where R is hydrogen or lower alkyl, NR'R" where R' and R" are independently hydrogen, lower alkyl, phenyl or phenyl substituted by lower alkyl, lower alkoxy, halogen, or trifluoromethyl; $R_2'$ and $R_3'$ are independently hydrogen, lower alkanoyl, benzoyl, or benzoyl substituted by lower alkyl, lower alkoxy, halogen, or trifluoromethyl, or when taken together, $R_2'$ and $R_3'$ may be lower alkylidene, such as isopropylidene; $R_6'$ is hydrogen, halogen or $R_5'O$ wherein $R_5'$ is hydrogen, lower alkanoyl, benzoyl, or benzoyl substituted by lower alkyl, lower alkoxy, halogen, or trifluoromethyl; and the ~NH— in the Formula IIB is attached to either one of the carbons adjacent; its individual diastereomers or mixtures thereof, or a pharmaceutically acceptable acid addition salt thereof.

The present invention also relates to a pharmaceutical composition comprising a therapeutically effective amount of a compound of the above Formula I with a pharmaceutically acceptable carrier, and to a method of treating mammals by administering to such mammals a dosage form of a compound of the Formula I as defined above.

DETAILED DESCRIPTION

In the compounds of the Formula I, the term "lower alkyl" is meant to include a straight or branched alkyl group having from 1 to 6 carbon atoms such as, for example, methyl, ethyl, propyl, isopropyl, butyl, sec-butyl, isobutyl, tert-butyl, amyl, isoamyl, neopentyl, hexyl, and the like.

Halogen includes particularly fluorine, chlorine or bromine.

Lower alkoxy is 0-alkyl from 1 to 6 carbon atoms as defined above for "lower alkyl."

Lower alkanoyl is a straight or branched

group of from 1 to 6 carbon atoms in the alkyl chain as defined above.

The term "and the ~NH— in the Formula IIB is attached to either one or the other of the adjacent carbons" means

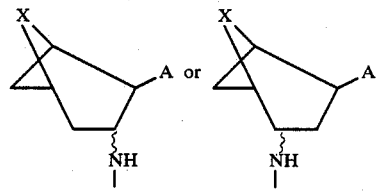

The compounds of Formula I are useful both in the free base form and in the form of acid addition salts. Both forms are within the scope of the invention. In practice, use of the salt form amounts to use of the base form. Appropriate pharmaceutically acceptable salts within the scope of the invention are those derived from mineral acids such as hydrochloric acid and sulfuric acid; and organic acids such as ethanesulfonic acid, benzenesulfonic acid, p-toluenesulfonic acid, and the like, giving the hydrochloride, sulfamate, ethanesulfonate, benzenesulfonate, p-toluenesulfonate, and the like, respectively.

The acid addition salts of said basic compounds are prepared either by dissolving the free base in aqueous or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The compounds of the invention may contain asymmetric carbon atoms. The invention includes the individual diastereomers, the pure S, the pure R isomer, and mixtures thereof. The individual diastereomers may be prepared or isolated by methods known in the art.

Under certain circumstances it is necessary to protect either the N or O of intermediates in the above noted process with suitable protecting groups which are known. Introduction and removal of such suitable oxygen and nitrogen protecting groups are well known in the art of organic chemistry; see for example, (1) "Protective Groups in Organic Chemistry," J. F. W. McOmie, ed., (New York, 1973), pp 43ff, 95ff; (2) J. F. W. McOmie, *Advances in Organic Chemistry*, Vol. 3, 191–281 (1963); (3) R. A. Borssonas, *Advances in Organic Chemistry*, Vol. 3, 159–190 (1963); and (4) J. F. W. McOmie, *Chem. & Ind.*, 603 (1979).

Examples of suitable oxygen protecting groups are benzyl, t-butyldimethylsilyl, methyl, isopropyl, ethyl, tertiary butyl, ethoxyethyl, and the like. Protection of an N-H containing moiety is necessary for some of the processes described herein for the preparation of compounds of this invention. Suitable nitrogen protecting groups are benzyl, triphenylmethyl, trialkylsilyl, trichloroethylcarbamate, trichloroethoxycarbonyl, vinyloxycarbamate, and the like.

Under certain circumstances it is necessary to protect two different oxygens with dissimilar protecting groups such that one can be selectively removed while leaving the other in place. The benzyl and t-butyldimethylsilyl groups are used in this way; either is removable in the presence of the other, benzyl being removed by catalytic hydrogenolysis, and t-butyldimethylsilyl being removed by reaction with, for example, tetra-n-butylammonium fluoride.

In the process described herein for the preparation of compounds of this invention the requirements for protective groups are generally well recognized by one skilled in the art of organic chemistry, and accordingly the use of appropriate protecting groups is necessarily implied by the processes of the charts herein, although not expressly illustrated.

The products of the reactions described herein are isolated by conventional means such as extraction, distillation, chromatography, and the like.

A preferred embodiment of the present invention is a compound of Formula I wherein $R_1$ is of Formula IIA; —NH— is either endo or exo; A, B, C, D, and E are all hydrogen; $R_2$ is hydrogen, $R_6'$ is chloro; and $R_2'$ and $R_3'$ are as defined above.

A particular embodiment includes $N_6$-endo-bicyclo[2.2.1]heptyladenosine, $N_6$-exo-bicyclo[2.2.1]heptyladenosine, and $N_6$-endo-bicyclo[2.2.1]heptyl-5'-chloroadenosine. The $N_6$-endo-bicyclo[2.2.1]heptyl-5'-chloroadenosine is the most preferred embodiment.

The compounds of Formula I may be conveniently synthesized by reacting a 6-halopurine riboside of Formula III with bicyclo amine of Formula IVA or IVB as shown hereinafter where A, B, C, D, E, and X is as defined above in an inert solvent such as alcohol, or an aprotic solvent such as dimethylformamide between about 25 to about 130° C. for from 1–48 hours. The bicyclo amines of Formula IVA or Formula IVB above are commercially available, may be made by known methods or may be made by methods analogous to those known in the art. It is useful to add a base such as triethylamine, or calcium carbonate to neutralize the hydrogen halide formed as a byproduct of the reaction, but this can also be accomplished by using an extra equivalent of the alkylamine. It is also convenient, although not necessary, to protect the ribofuranose hydroxyl groups as acetate or benzoate esters which can be removed with ammonium hydroxide or sodium methoxide following the synthesis of the $N^6$-substituted adenosine. The reaction is illustrated as follows:

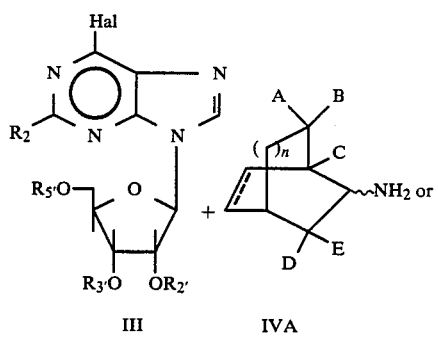

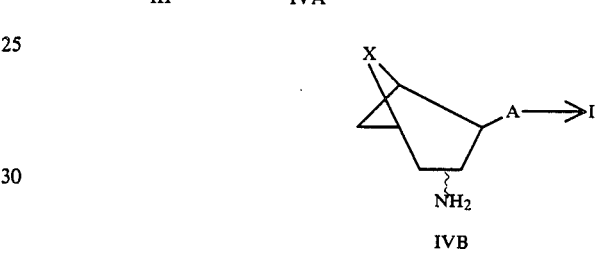

wherein $R_{6'}$ is $R_{5'}O$ wherein Hal is halogen, preferably chlorine or bromine, and A, B, C, D, E, $R_2$, $R_2'$, $R_3'$, and $R_5'$ are as defined for Formula I.

In addition, compounds of formula I wherein $R_6'$ is halogen may also be prepared from a compound Formula I where $R_6'$ is $R_5'O$ where $R_2'$, $R_3'$, and $R_5'$ are all hydrogen, in a stepwise manner, by first reacting with the compound to form a protecting group for the oxygen of $OR_2'$ and $OR_3'$, i.e., where $R_2'$ and $R_3'$ are other than hydrogen, e.g., dimethoxy propane, in acetone to give a compound of Formula I having protected groups followed by chlorinating the 5'-hydroxymethyl using thionyl chloride in tetrahydrofuran, and removing the protecting group under aqueous acid condition using acids, for example, hydrochloric, acetic, sulfuric, and the like as illustrated below.

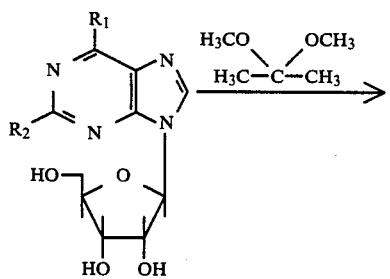

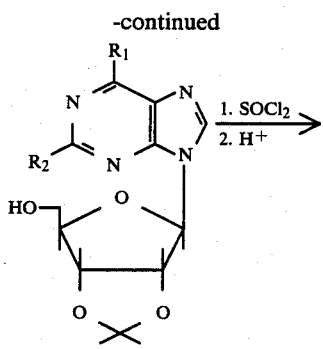

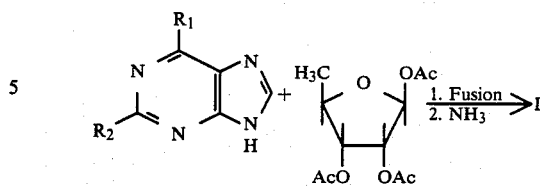

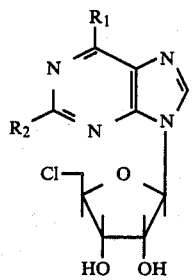

In addition, compounds of Formula I wherein $R_2$ is other than hydrogen or halogen, may also be prepared from 2,6-dichloropuripe riboside triacetate of Formula V in a stepwise manner, by first reacting a compound of the Formula V with bicycloamine of Formula IVa or IVb to give a compound of Formula VI, followed by replacing the chlorine atom at $C_2$ with the group $R_2$ using nucleophilic displacement conditions, and removing a protecting group, i.e., the acetate, as illustrated below.

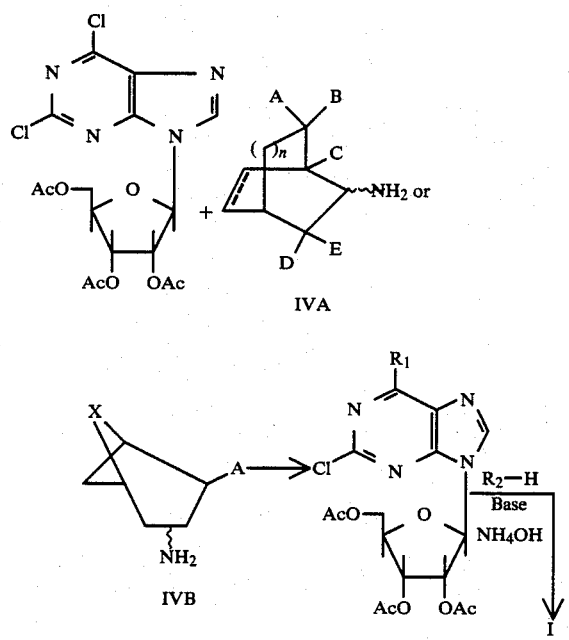

The compounds of Formula I wherein $R_6'$ is hydrogen are prepared according to the following scheme:

Generally the conditions of the above scheme are analogous to those known in the art.

The compounds of Formula I have been found to possess differing affinities for adenosine receptors (designated $A_1$ and $A_2$ receptors for convenience). These compounds are active in animal tests as having analgesic properties and as such, are useful in the treatment of pain and inflammation.

PHARMACOLOGICAL EVALUATION

Adenosine Receptor Binding—$A_1$ Receptor Affinity (RBA1)

Preparation of Membranes

Whole brain minus cerebellum and brainstem from male Long Evans rats (150–200 g) was homogenized in 30 volumes of ice-cold 0.05M Tris-HCl buffer pH 7.7 using a Brinkman Polytron PT-10, (setting number 6 for 20 seconds) and centrifuged for ten minutes at 20,000×g (Sorvall RC-2), 4° C. The supernatant was discarded, and the pellet was resuspended and centrifuged as before. The pellet was resuspended in 20 ml Tris-HCl buffer containing two International Units/ml of adenosine deaminase (Sigma type III from calf intestinal mucosa), incubated at 37° C. for 30 minutes, then subsequently at 0° C. for ten minutes. The homogenate was again centrifuged, and the final pellet was resuspended in ice-cold 0.05M Tris-HCl buffer pH 7.7 to a concentration of 20 mg/ml original wet tissue weight and used immediately.

Assay Conditions

Tissue homogenate (10 mg/ml) was incubated in 0.05M Tris-HCl buffer pH 7.7 containing 1.0 nM [$^3$H]-$N^6$-cyclohexyladenosine ([$^3$H]-CHA) with or without test agents in triplicate for one hour at 25° C. Incubation volume was 2 ml. Unbound [$^3$H]-CHA was separated by rapid filtration under reduced pressure through Whatman glass fiber (GF/B) filters. The filters were rinsed three times with 5 ml of ice cold 0.05M Tris-HCl buffer pH 7.7. The radiolabeled ligand retained on the filter was measured by liquid scintillation spectrophotometry after shaking the filters for one hour or longer on a mechanical shaker in 10 ml of Beckman Ready-Solv HP scintillation cocktail.

Calculations

Nonspecific binding was defined as the binding which occurred in the presence of 1 mM theophylline. The concentration of test agent which inhibited 50% of the specific binding (IC$_{50}$) was determined by nonlinear computer curve fit. The Scatchard plot was calculated by linear regression of the line obtained by plotting the amount of radioligand bound (pmoles/gram of tissue) versus $$\left[ \frac{\text{bound radioligand}}{\text{free radioligand}} \right].$$

Since the amount of radioligand bound was a small fraction of the total amount added, free radioligand was defined as the concentration (nM) of radioligand added to the incubation mixture. The Hill coefficient was calculated by linear regression of the line obtained by plotting the log of the bound radioligand vs the log of the $$\left[ \frac{\text{bound radioligand}}{B_{max} - \text{bound radioligand}} \right].$$

The maximal number of binding sites ($B_{max}$) was calculated from the Scatchard plot.

Adenosine Receptor Binding—$A_2$ Receptor Affinity (RBA2)

Tissue Preparation

Brains from 200–500 g mixed sex Sprague-Dawley rats were purchased from Pel-Freez (Rogers, Arkansas). Fresh brains from male Long-Evans hooded rats (Blue Spruce Farms, Altamont, NY) gave essentially identical results. Brains were thawed and then kept on ice while the striata were dissected out. Striata were disrupted in 10 vol of ice-cold 50 mM Tris.HCl (pH 7.7 at 25° C., pH 8.26 at 5° C.) (Tris) for 30 seconds in a Polytron PT-10 (Brinkmann) at setting 5. The suspension was centrifuged at 50,000×g for ten minutes, the supernatant discarded, the pellet resuspended in 10 vol ice-cold Tris as above, recentrifuged, resuspended at 1 g/5 ml, and stored in plastic vials at −70° C. (stable for at least six months). When needed, tissue was thawed at room temperature, disrupted in a Polytron, and kept on ice until used.

Incubation Conditions

All incubations were for 60 minutes at 25° C. in 12×75 mm glass tubes containing 1 ml Tris with 5 mg original tissue weight of rat weight of rat striatal membranes, 4 nM [$^3$H]-N-ethyl adenosine-5'-carboxamide ([$^3$H]NECA), 50 nM $N^6$-cyclopentyladenosine (to eliminate $A_1$ receptor binding), 10 mM mgCl$_2$, 0.1 units/ml of adenosine deaminase and 1% dimethylsulfoxide. $N^6$-Cyclopentyladenosine was dissolved at 10 mM in 0.02N HCl and diluted in Tris. Stock solutions and dilutions of $N^6$-cyclopentyladenosine could be stored at −20° C. for several months. Test compounds were dissolved at 10 mM in dimethylsulfoxide on the same day as the experiment, and diluted in dimethylsulfoxide to 100× the final incubation concentration. Control incubations received an equal volume (10 μl) of dimethylsulfoxide; the resulting concentration of dimethylsulfoxide had no effect on binding. [$^3$H]NECA was diluted to 40 nM in Tris. The membrane suspension (5 mg/0.79 ml) contained sufficient MgCl$_2$ and adenosine deaminase to give 10 mM and 0.1 units/ml, respectively, final concentration in the incubation. For test compounds with IC$_{50}$ values less than 1 1 μM, the order of additions was test compound (10 μl), $N^6$-cyclopentyladenosine (100 μl), [$^3$H]NECA (100 μl), and membranes (0.79 ml). For test compounds with IC$_{50}$ values greater than 1 μM and limited water solubility, the order of additions (same volumes) was test compound, membranes, $N^6$-cyclopentyladenosine, and [$^3$H]NECA. After all additions, the rack of tubes was vortexed, and the tubes were then incubated for 60 min at 25° C. in a shaking water bath. The rack of tubes was vortexed an additional time halfway through the incubation.

Incubations were terminated by filtration through 2.4 cm GF/B filters under reduced pressure. Each tube was filtered as follows: the contents of the tube were poured onto the filter, 4 ml of ice-cold Tris were added to the tube and the contents poured onto the filter, and the filter was washed twice with 4 ml of ice-cold Tris. The filtration was complete in about twelve seconds. Filters were put in scintillation vials, 8 ml of Formula 947 scintillation fluid added, and the vials left overnight, shaken, and counted in a liquid scintillation counter at 40% efficiency.

Data Analysis

Nonspecific binding was defined as binding in the presence of 100 μM $N^6$-cyclopentyladenosine, and specific binding was defined as total binding minus nonspecific binding. The IC$_{50}$ was calculated by weighted nonlinear least squares curve-fitting to the mass-action equation.

$$Y = T - S \cdot \frac{D}{D + K}$$

where
Y is cpm bound
T is cpm total binding without drug
S is cpm specific binding without drug
D is the concentration of drug and
K is the IC$_{50}$ of the drug Weighting factors were calculated under the assumption that the standard deviation was proportional to the predicted value of Y. Nonspecific binding was treated as a very large (infinite) concentration of drug in the computer analysis.

The IC$_{50}$ values (nM) for adenosine $A_1$ and $A_2$ receptor affinity are reported in the table.

ANALGESIC EVALUATION

The antiwrithing (AW) test provides preliminary assessment of compounds with potential analgesic activity. The test is performed in male Swiss-Webster mice. Compounds are administered subcutaneously in aqueous 0.2% methylcellulose or other appropriate vehicles in volumes of 10 ml/kg. Dosages represent active moiety.

Acetic acid (0.6%, 10 ml/kg) is injected intraperitoneally 20 minutes after administration of the adenosine agonist. Writhing movements are counted for five minutes starting seven minutes after the acetic acid injection. Writhing is defined as abdominal constriction and stretching of the body and hind legs with concave arching of the back. Data are expressed as ED$_{50}$ values, where the ED$_{50}$ is the dose necessary to suppress writhing by 50% relative to vehicle controls. ED$_{50}$ values are calculated by nonlinear regression analysis.

ANTIINFLAMMATORY ASSAY

Assessment of immunoinflammatory or antiinflammatory activity is provided by the carrageenan pleurisy assay. Carrageenan pleurisy is induced as previously described by Carter, G. W., et al., in J. Pharm. Pharmacol 34:66–67, 1982. Carrageenan (310 μg/rat) is injected intrapleurally in a 0.25 ml volume of pyrogen-free saline. Four hours later, the rats are sacrificed and 2 ml of a phenol red solution (325 mg phenol red in 1 liter of 0.05M phosphate buffered saline) are added to each pleural cavity. The contents of the cavities are mixed and transferred to glass test tubes. A 50 μl aliquot is removed from each tube and exudate cells are counted after red blood cells lysis (with Zapoglobin; Coulter Electronics, Hialeah FL) using a Coulter model ZBI counter. The remaining exudate-phenol red mixture is centrifuged at 750×g for 15 minutes. One hundred μl of the supernatent fluid is diluted with 3.9 ml of phosphate buffer (0.072M of tribasic sodium phosphate, $Na_3PO_4.12H_2O$, in water) and the absorbance is measured at 560 nm.

Exudate volume is calculated as follows:

$$V_1 = \frac{V2(A_2 - A_3)}{(A_3 - A_1)}$$

where $V_1$=unknown volume of exudate, $V_2$=volume of dye added to cavity (2 ml), $A_1$=absorbance of exudate (assumed to be zero), $A_2$=absorbance of the phenol red solution, $A_3$=absorbance of exudate and phenol red solution.

Inhibition of exudate or formation is calculated by the following equations:

% inhibition (exudate) =

$$\frac{\text{Vehicle Exudate Volume} - \text{Inhibitor Exudate}}{\text{Vehicle Exudate Volume}} \times 100$$

% inhibition (cell count) =

$$\frac{\text{Vehicle Cell Count} - \text{Inhibitor Cell Count}}{\text{Vehicle Cell Count}} \times 100$$

$ID_{50}$ values are calculated by Probit analysis.

The compound of Example 1 was administered one hour prior to carrageenan injection.

The biological data are summarized in the Table. Accordingly, the present invention also includes a pharmaceutical composition for treating pain, and inflammation comprising a corresponding analgesic or antiinflammatory effective amount of a compound of the Formula I as defined above together with a pharmaceutically acceptable carrier.

| | Receptor Binding | |
|---|---|---|
| Example | RBA-1 (nM) | RBA-2 (nM) |
| 1 | 0.85 | 1300 |
| 2 | 1.4 | 1400 |
| 5 | 0.69 | 3093 |

| AW Test (Analgesic Test) | |
|---|---|
| Example | AW ED$_{50}$ mg/kg |
| 1 | 0.03 |

| Carrageenan Pleurisy Assay (Immunoinflammatory Test) | | |
|---|---|---|
| | ID$_{50}$ (mg/kg) | |
| Example | Exudate | WBC |
| 1 | 0.15 | 0.12 | or specifically for various doses as follows:

| Carrageenan Pleurisy Assy | | | |
|---|---|---|---|
| | Dose | % Inhibition | |
| Example | mg/kg | Exudate | WBC |
| 1 | 0.1 | 49.3 | 74.1 |
| | 0.2 | 60.0 | 70.0 |
| | 0.4 | 81.3 | 90.0 |
| | 0.8 | 42.7 | 68.4 |
| 2 | 0.3 | 24.3 | 25.7 |
| | 1.0 | 22.9 | 52.9 |
| 5 | 0.1 | 11.7 | 18.4 |
| | 0.3 | 16.8 | 40.0 |

The present invention further includes a method for treating pain or inflammation in mammals suffering therefrom comprising administering to such mammals either orally or parenterally a corresponding pharmaceutical composition containing a compound of the Formula I as defined above in appropriate unit dosage form.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solublizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 1 mg to 500 mg preferably to 5 to 100 mg according to the particular application and the potency of the active ingredient. The compositions can, if desired, also contain other compatible therapeutic agents.

In therapeutic use as described above, the mammalian dosage range for a 70 kg subject is from 0.1 to 150 mg/kg of body weight per day or preferably 1 to 50 mg/kg of body weight per day. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The following Examples further illustrate the invention.

EXAMPLE 1

N$^6$-endo-Bicyclo[2.2.1]heptyl adenosine

A mixture of 4.0 g of 6-chloropurine riboside, 2.57 g endo-2-aminonorbornane hydrochloride and 3.53 g triethylamine is refluxed in 100 ml ethanol under nitrogen for 20 hours. The solvent is evaporated to dryness. Residual solid material is dissolved in minimum of 2-propanol and diluted with excess cold water. Clear aqueous solution is decanted off. The residual solid is dissolved in ethanol and volatiles are evaporated. This is repeated once more yielding 3.8 g (75%) of N-6-endobicyclo[2.2.1]heptyladenosine having a melting point of 128°–130° C.

Analysis calculated for $C_{17}H_{23}N_5O_4$: C, 56.49; H, 6.41; N, 19.37; Found: C, 56.44; H, 6.81; N, 18.78.

EXAMPLE 2

N$^6$-exo-Bicyclo[2.2.1]heptyladenosine

A mixture of 4.0 g of 6-chloropurine riboside, 1.8 g exo-2-aminonorbornane and 2.1 g of triethylamine is refluxed in 100 ml ethanol under nitrogen for 20 hours. The solvent is evaporated to dryness. The residual solid is treated with 50 ml of cold H$_2$O. Clear aqueous solution is decanted off and the solid material is dissolved in ethanol. Volatiles are evaporated under vacuo. This is repeated twice yielding solid material which is crystallized from ethanolethyl acetate-hexane affording 4.1 g (81%) of N$^6$-exo-bicyclo[2.2.1]heptyladenosine having a melting point of 110°–112° C.

Analysis calculated for $C_{17}H_{23}N_5O_4$: C, 56.49; H, 6.41; N, 19.37; Found: C, 55.88; H, 5.89; N, 18.59.

EXAMPLE 3

N$^6$-2-(endo)-norbornyl-2',3'-O-isopopylidene adenosine

N$^6$-2-(endo)norbornyladenosine (12.7 g, 35 mmol), 2,2-dimethoxy propane (35 ml) and bis-p-nitrophenylphosphate hydrate (12.8 g, 38 mmol) were stirred in acetone (150 ml) at room temperature 18 hours. The reaction was quenched with 0.1N NaHCO$_3$ (100 ml) and stirred for one hour. The acetone was evaporated in vacuo and the aqueous solution extracted with methylene chloride (200 ml). The organics were dried over magnesium sulfate and evaporated in vacuo to give an off white foam. The foam was dissolved in methanol (100 ml) and poured through a plug of Dowex 1×8 (NaHCO$_3$ form) resin. The resin was washed with methanol (300 ml) and the combined filtrates evaporated in vacuo to give 10.6 g (75%) of a white solid, mp 90°–98° C.

Analysis calculated for $C_{20}H_{27}N_5O_4$: C, 59.84; H, 6.78; N, 17.45; Found: C, 59.48; H, 6.71; N, 17.24.

EXAMPLE 4

N$^6$-2-(endo)-norbornyl-5'-chloro-5'-deoxy-2',3'-O-isopropylidene adenosine

The isopropylidene analog, as prepared in Example 3 above, (6.3 g, 15.7 mmol) was stirred in THF (100 ml) and treated with thionylchloride (2.8 g, 23.5 mmol). The reaction stirred at room temperature, overnight. The solvent was evaporated in vacuo and the residue dissolved in methylene chloride (100 ml), and washed with water (2×100 ml). The organic dried over magnesium sulfate and evaporated in vacuo. The residue dissolved in ethyl acetate (25 ml) and purified by prep 500A chromatography (silica gel, 1 column, 100 ml/min). The slow running fraction was isolated by evaporation of solvent to give 4.4 g (67%) of a white foam, mp 61°–70° C. Analysis calculated for $C_{20}H_{26}ClN_5O_3$: C, 57.20; H, 6.24; N, 16.68; Cl, 8.44; Found: C, 56.97; H, 6.13; N, 16.59; Cl, 8.62.

EXAMPLE 5

N⁶-2-endo-norbornyl-5'-chloro-5'-deoxy-adenosine

The 5'-chloro-isopropylidene analog, as prepared in Example 4 above, (4.3 g, 10.2 mmol) was stirred in 50% formic acid (100 ml) at 50° C. for four hours. The acid was evaporated in vacuo and the residue coevaporated with methanol (2×50 ml) to give an off-white foam. The foam was dissolved in acetone (25 ml) and purified by prep 500A chromatography (silica gel, 1 column, 100 ml/min). The major refraction index active fraction was isolated by evaporation of solvent to give 2.4 g (62%) of a white solid, mp 96°–99° C.

Analysis calculated for $C_{17}H_{22}ClN_5O_3$: C, 53.75; H, 5.84; N, 18.44; Found: C, 53.89; H, 6.05; N, 18.23.

EXAMPLE 6

N⁶-(endo)norbornyl-5'-deoxyadenosine

Six chloropurine (2.3 g, 15 mmol), triethyl amine (3.5 g, 35 mmol) and 2-endo-aminonorbornane hydrochloride (2.5 g, 17 mmol) were stirred at reflux in 100 ml of ethanol for 72 hours. The solution was cooled to room temperature and the ethanol was evaporated in vacuo. The residue was dissolved in chloroform and washed with water (100 ml). The organics were dried over magnesium sulfate and the solvent was evaporated in vacuo. The residue was dried at 65° C. in vacuo overnight to give 2.1 g (62%) of a light green solid, mp 217°–219° C.

The adenine (4.4 g, 19.1 mmol) and 5' deoxy ribose (6.1 g, 23 mmol) were melted and stirred at 200° C. To the melt was added one micro drop of concentrated sulfuric acid and the acetic acid formed was removed in a gentle stream of nitrogen. The solution was stirred for four hours before cooling to room temperature. The glassy residue was broken up in 100 ml of ethyl acetate in an ultrasonic bath. The solution was then purified by chromatography to give after evaporation of the solvent 1.6 g of an off-white foam, identified in Example 7 hereinafter. The foam (1.4 g, 3.3 mmol) was then dissolved in 100 ml of methanolic ammonia (saturated at 0° C.) and the solution was stirred at room temperature for six hours. The solution was evaporated in vacuo and the residue purified by chromatography to give, after evaporation of solvent 0.9 g (18%) of a hygroscopic white solid, mp 93°–101° C.

EXAMPLE 7

N⁶-Endo-norbornyl-5'-deoxyadenosine-2',3'-di-O-acetyl

Compound 7 from Example 6 was analyzed to give the product N⁶-(2-endo-norbornyl)-5'-deoxy-2',3'-diacetyl adenosine 1.6 g (19.5%), mp 68°–77° C.

Analysis calculated for $C_{21}H_{27}N_5O_5$: C, 58.34; H, 6.60; N, 14.79; Found: C, 58.32; H, 6.48; N, 14.86.

I claim:
1. A compound of the formula

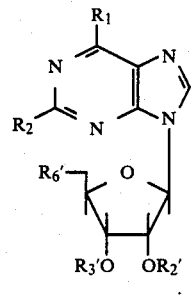

wherein $R_1$ is of formula

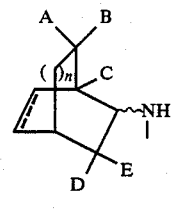   IIA or

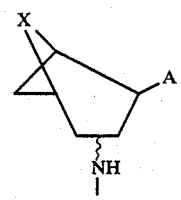   IIB in which NH— is either endo or exo; ------ is a double or single bond; n is zero, one, or two; A and B are either both hydrogen or both methyl; D and E are also either both hydrogen or both methyl; C is hydrogen or methyl; and the proviso that when D and E are methyl then A and B are both hydrogen and C is methyl but when D and E are hydrogen then A, B, and C are all hydrogen or all methyl; X is —C(CH₃)₂—, —CH₂—, —CH₂CH₂—, or —CH=CH; $R_2$ is hydrogen, halogen, SR where R is hydrogen or lower alkyl, $NR^i R^{ii}$ where $R^i$ and $R^{ii}$ are independently hydrogen, lower alkyl, phenyl or phenyl substituted by lower alkyl, lower alkoxy, halogen, or trifluoromethyl; $R_2'$ and $R_3'$ are independently hydrogen, lower alkanoyl, benzoyl, or benzoyl substituted by lower alkyl, lower alkoxy, halogen, or trifluoromethyl, or when taken together, $R_2'$ and $R_3'$ may be lower alkylidene; $R_6'$ is halogen, hydrogen or $R_5.O$ where $R_5'$ is hydrogen, lower alkanoyl, benzoyl, or benzoyl substituted by lower alkyl, lower alkoxy, halogen, or trifluoromethyl; and the ~NH— is attached to either one or the other of the adjacent carbons; its individual diastereomers or mixtures thereof, or a pharmaceutically acceptable acid addition salt thereof.

2. A compound as claimed in claim 1, wherein $R_2$ is hydrogen.

3. A compound as claimed in claim 1, wherein $R_1$ is of the Formula IIA.

4. A compound as claimed in claim 1, wherein $R_1$ is of the Formula IIB.

5. A compound as claimed in claim 3 and which is N⁶-endo-bicyclo[2.2.1]heptyladenosine.

6. A compound as claimed in claim 3 which is N⁶-exo-bicyclo[2.2.1]heptyladenosine.

7. A compound as claimed in claim 3 which is $N^6$-endo-bicyclo[2.2.1]heptyl-5'-chloro-5'-deoxyadenosine.

8. A compound as claimed in claim 3 which is $N^6$-(endo)-norbornyl-5'-deoxyadenosine.

9. A compound as claimed in claim 3 which is $N^6$-(2-endo-norbornyl)-5'-deoxy-2',3'-diacetyladenosine.

10. A compound as claimed in claim 3 which is $N^6$-norbornyl-2',3'-O-isopropylideneadenosine.

11. A compound as claimed in claim 3 which is $N^6$-2-(endo)-norbornyl-5'-chloro-5'-deoxy-2',3'-O-isopropylidene adenosine.

12. a pharmaceutical composition for treating pain or inflammation comprising an analgesic or antiinflammatory effective amount of a compound as claimed in claim 1 together with a pharmaceutically accepted carrier.

13. A method for treating pain in a mammal suffering therefrom, which comprises administering to such mammal an analgesic effective amount of a compound as claimed in claim 1 in unit dosage form.

14. A method for treating inflammation in a mammal suffering therefrom, which comprises administering to such mammal an antiinflammatory effective amount of a compound as claimed in claim 1 in unit dosage form.

* * * * *

UNITED STATES PATENT AND TRADEMARK OFFICE
CERTIFICATE OF CORRECTION

PATENT NO. : 4,714,697

DATED : December 22, 1987

INVENTOR(S) : Bharat Trivedi

It is certified that error appears in the above—identified patent and that said Letters Patent is hereby corrected as shown below:

Column 14, line 52, change "$R_5.O$" to --$R_5, O$--

Signed and Sealed this

Tenth Day of May, 1988

Attest:

Attesting Officer

DONALD J. QUIGG

Commissioner of Patents and Trademarks